US009383340B1

(12) United States Patent
Malocha et al.

(10) Patent No.: US 9,383,340 B1
(45) Date of Patent: Jul. 5, 2016

(54) PASSIVE, WIRELESS, SURFACE ACOUSTIC WAVE IDENTIFICATION TAG WITH HYDROGEN GAS SENSOR

(71) Applicant: University of Central Florida Research Foundation, Inc., Orlando, FL (US)

(72) Inventors: Donald Malocha, Winter Park, FL (US); Brian Fisher, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 524 days.

(21) Appl. No.: 13/780,098

(22) Filed: Feb. 28, 2013

(51) Int. Cl.
*G01N 29/02* (2006.01)

(52) U.S. Cl.
CPC .............. *G01N 29/02* (2013.01); *G01N 29/022* (2013.01); *G01N 2291/0423* (2013.01)

(58) Field of Classification Search
CPC ................. G01N 29/02; G01N 29/022; G01N 2291/0423
USPC .................................. 73/23.2, 24.01; 338/34
See application file for complete search history.

(56) References Cited

U.S. PATENT DOCUMENTS

| 7,047,792 | B1 | 5/2006 | Bhethanabotla | |
|---|---|---|---|---|
| 7,268,662 | B2 | 9/2007 | Hines | |
| 7,777,625 | B1 * | 8/2010 | Puccio et al. | 340/572.1 |

OTHER PUBLICATIONS

De, et al., Nanocrystalline Mesoporous Palladium Activated Tin Oxide Thin Films as Room-Temperature Hydrogen Gas Sensors, The Royal Society of Chemistry, 2007, pp. 1840-1842.
Fisher, et al., A Study on the Aging of Ultra-Thin Palladium Films on SAW Hydrogen Gas Sensors, IEEE, 2010, pp. 242-247.
Fisher, et al., Cryogenic Liquid Sensing Using SAW Devices, IEEE, 2007, pp. 505-510.
Kasthurirengan, et al., Palladium Doped Tin Oxide Based Hydrogen Gas Sensors for Safety Applications, Advances in Cryogenic Engineering, 2010, pp. 1239-1246.
Fisher, et al., Study of the Acoustoelectric Effect for SAW Sensors, IEEE, 2010, pp. 698-706, vol. 57, No. 3.
Fisher, et al., SAW-Thin-Film Acoustoelectric In-Situ Observation and Measurement, 6 pages.
Oommen, et al., Characteristics of Electron Beam Evaporated and Electrodeposited Cu2O Thin Films—Comparative Study, Int. J. Electrochem. Sci., 2012, pp. 8288-8298, vol. 7.
Fisher, et al., In Situ Observation and Measurement of the SAW Thin-Film Acoustoelectric Effect, IEEE, 2012, pp. 472-480, vol. 59, No. 3.
Vanotti, et al., Surface Acoustic Wave Devices Exploiting Palladium Layer Properties for Selective Detection of Hydrogen, Sensor Devices, 2012, pp. 143-147.
Jakubik, et al., Surface Acoustic Wave Hydrogen Gas Sensor Based on Layered Structure of Palladium/Metal-Free Phthalocyanine, Bulletin of the Polish Academy of Sciences Technical Sciences, 2008, pp. 133-138, vol. 56, No. 2.

(Continued)

*Primary Examiner* — Hezron E Williams
*Assistant Examiner* — David Z Huang
(74) *Attorney, Agent, or Firm* — Jetter & Associates, P.A.

(57) ABSTRACT

Methods, systems and devices for a coded SAW tag and hydrogen gas sensor with substrate, detector and identical reference bank of reflectors fabricated the substrate to generate a surface acoustic wave in response to a interrogation signal, a transducer between the detector and reflectors, and a tin dioxide ($SnO_2$) and palladium (Pd) film sensitive to hydrogen gas at ambient temperature deposited in a propagation delay path between the reflectors and the transducer to modulate the detector surface acoustic wave propagation parameters in response to sensing a hydrogen gas. The SnO2 and Pd film is deposited on the delay path by depositing the film through a mask. The deposited film is annealed to gain room-temperature hydrogen sensitivity and reversibility.

8 Claims, 7 Drawing Sheets

(56) References Cited

OTHER PUBLICATIONS

Huang, et al., A Room Temperature Surface Acoustic Wave Hydrogen Sensor with Pt Coated ZnO Nanorods, Nanotechnology, 2009, pp. 1-6.

Yamanaka, et al., Ball Saw Device for Hydrogen Gas Sensor, IEEE Ultrasonics Symposium, 2003, pp. 299-302.

De, et al., Nanocrystalline Mesoporous Palladium Activated Tin Oxide Thin Films as Room-Temperature Hydrogen Gas Sensors, Chem. Commun., 2007, pp. 1840-1842.

* cited by examiner

PASSIVE, WIRELESS, SURFACE ACOUSTIC WAVE IDENTIFICATION TAG WITH HYDROGEN GAS SENSOR

FIELD OF THE INVENTION

This invention relates to surface acoustic wave devices and, in particular, to methods, systems and devices for passive, wireless, surface acoustic wave identification tags with a tin-oxide and palladium thin film hydrogen gas sensor in the propagation path between the tag transducers and the frequency coded reflector banks.

BACKGROUND AND PRIOR ART

Hydrogen gas is colorless, odorless, and not detectable by human senses. It is lighter than air and hence difficult to detect and is it not detectable by available infrared gas sensing technology. Coupled with the challenge of detection are the safety risks posed by the gas itself.

Hydrogen gas molecules are small and can diffuse through many materials considered airtight. Constant long-term exposure to hydrogen causes a phenomenon known as "hydrogen embrittlement" in many materials including metals and plastics. Embrittlement reduces the ductility and tensile strength of containment vessels to the point of fracture and eventual rupture and makes hydrogen more difficult to contain than other gasses. A form of H2 embrittlement takes place by chemical reaction. At high temperatures, hydrogen reacts with one or more components of metal walls to form hydrides, which weaken the atomic lattice.

Hydrogen gas is colorless, odorless, and not detectable by human senses. It is lighter than air and hence difficult to detect where accumulations cannot occur, and is it not detectable by infrared gas sensing technology. Coupled with the challenge of detection are the safety risks posed by the gas itself. At 1 atm, fire hazards exist for $H_2$—$O_2$ mixtures between the lower flammability limit (LFL) of 4% and upper flammability limit (UFL) of 94% $H_2$ by volume. In air, the lower and upper flammability limit of $H_2$ is 4.1% and 75% $H_2$ by volume, respectively, as shown in FIG. 7 because the $O_2$ composition of air is only 21%.

The lower and upper flammability limit and is also temperature dependent. The minimum ignition energy required to ignite hydrogen gas is between only 0.017 mJ to 1 mJ at 1 atm depending on hydrogen gas concentration in air, and decreases as temperature is increased. In comparison, the typical static electric discharge caused by humans in normal activity and industrial machinery lie the range of 1-100 mJ, thus, all personnel in an enclosed area must be evacuated before the $H_2$ concentration in air reaches the lower flammability limit.

Current commercially available hydrogen gas detection technologies include catalytic, thermal conductivity, electro-mechanical, resistance based technology, work-function based technology, and optical detectors. Of the commercially available sensor technologies, only resistance and work-function based technologies can be integrated with a compact low-power wireless platform. Acoustic technologies can also be implemented in a passive, wireless configuration, however, none are commercially available.

The operating temperature of solid-state gas sensors is in the range of 50 to 150° C. and is not as hazardous as a catalytic bead sensor. However, the probability of spark discharges increases as humidity decreases and for a given moisture content, humidity is approximately halved for a 10 degree rise in temperature. This suggests that a sensor that operates at elevated temperatures increases the probability of hydrogen combustion via decreasing the minimum ignition energy, the lower flammability limit and increasing the probability of spark discharge.

Another problem with prior art sensor technologies is reversible detection of hydrogen gas at room temperature is difficult because the activation energy required to desorb the hydrogen gas from the sensitive film is a high temperature. Most commercially available hydrogen gas sensors use localized heaters that control the operating temperature, which is typically greater than 300° C. for catalytic bead gas sensors and 50 to 150° C. for solid-state gas sensors. The localized heaters require relatively high constant current, which translates to a limited battery life of the sensor.

The use of surface acoustic wave (SAW) devices as sensors was introduced in the 1970's. The first SAW based hydrogen sensor was demonstrated by D'Amico et al. in 1982. D'Amico utilized SAW single and dual delay line oscillators in order to observe the frequency shift due to mass loading caused by a thick palladium (Pd) film in a range of 1900-7600 Å in the delay path. The fractional change in frequency was found to be proportional to film thickness. The reaction rates ranged from 0.8 to 21 Hz per second depending on gas concentration and flow rate.

Jakubik et al. also implemented a SAW dual delay line oscillator for hydrogen gas sensing, with the distinction of using a bilayer structure in the delay path. The bi-layer structure included a 1200 Å dielectric film consisting of copper phthalocycanine, (CuPc), nickel phthalocycanine, (NiPc), or metal-free phthalocycanine, ($H_2$Pc). The structure was placed between the SAW substrate and a 200 Å Pd film. The dielectric prevented the Pd film from shorting out the acoustoelectric response of the SAW. The mass loading effect of hydrogenated CuPc, NiPc, and $H_2$Pc and 200 Å Pd films are small when compared to the electrical response, thus, the acoustoelectric response is the dominant sensing mechanism.

The devices designed by D'Amico and Jakubik are active and wired and comprise a majority of the SAW-based hydrogen sensing designs found in literature.

A third example is the ball SAW device described in K. Yamanaka, et al., "Ball SAW Device For Hydrogen Gas Sensor," presented at the IEEE Ultrasonics Symposium, 2003. Like D'Amico, the ball sensor used a 200 Å Pd film in the SAW propagation path. Although, the ball sensor could be configured as a wireless device, the design was relatively complex and expensive to fabricate.

Wireless hydrogen sensors have been demonstrated by Y.-S. Huang, Y.-Y. Chen, and T.-T. Wu, "A passive wireless hydrogen surface acoustic wave sensor based on Pt-coated ZnO nanorods," Nanotechnology, vol. 21, 2010 used a $H_2$ sensitive resister to modulate a fraction of energy that is reflected by the SAW interdigitated transducer when the resister was exposed to hydrogen gas. Problems associated with Huang H2 sensors include long response time and the devices were not coded, thus when more than one was used, there was no way to distinguish one from another.

Other know hydrogen detectors include U.S. Pat. No. 7,268,662 issued to Hines, et al., on Sep. 11, 2007 which teaches use of a palladium nanocluster thin film deposited on the monolayer an interdigital SAW transducer to cause a modification of a response signal due to a change in conductivity of the palladium film when exposed to hydrogen; and U.S. Pat. No. 7,047,792 issued to Bhethanabotla, et al., on May 23, 2006 teaches nanoparticles or nanowires of palladium and metal free pthalocyanine coated on a lithium niobate substrate of a SAW device delay line.

Articles and papers on the subject include Ralf Kohn, et al, Nanocrystalline mesoporous palladium activated tin oxide thin films as room temperature hydrogen gas sensors, from The Royal Society of Chemistry, 2007 which reports a surfactant-directed assembly approach to form high surface area mesoporous Pd-doped $SnO_2$ films exhibiting an interconnected nanocrystalline structure and high sensitivity for hydrogen gas at room temperature. Another paper by S. Kasthurirengan, et al., Palladium doped tin oxide based hydrogen gas sensors for safety applications AIP Conf. Proc. 1218, 1239 (2010) discloses development of Pd-doped tin-oxide-based hydrogen gas sensors.

The problems associated with the prior art devices described above can be mitigated by the implementation of a wireless, room-temperature hydrogen gas detection system, which continuously monitors multiple nodes and reports temperature and hydrogen gas presence. The ideal solution to the problems includes SAW device coding to determine which SAW device in a multi-tag system detects the hydrogen.

SUMMARY OF THE INVENTION

A primary objective of the present invention is to provide methods, systems and devices for a wireless surface acoustic wave radio frequency device with a hydrogen gas sensor coupled in the path between the surface acoustic wave reflector bank and the transceiver.

A secondary objective of the present invention is to provide methods for creating a tin doxide (SnO2) and palladium (Pd) thin-film stack that is sensitive to hydrogen gas at room temperature for use with a surface acoustic wave identification tags.

A third objective of the present invention is to provide methods, systems and devices for a wireless hydrogen gas sensor via the integration of the SnO2-Pd film with the orthogonal frequency coded surface acoustic wave platform.

A fourth objective of the present invention is to provide methods, systems and devices for a low power or battery less, wireless surface acoustic wave radio frequency device with a hydrogen gas sensor.

A first embodiment provides a method for fabricating a tin-dioxide (SnO2) and palladium (Pd) film that can be sensitive to hydrogen gas at room temperature by providing a surface acoustic wave (SAW) tag having a reference and a detector bank of sequential reflectors coupled with a transducer and a delay patch between the detector bank of reflectors and the transducer on a substrate, masking the SAW tag to expose the delay path, and depositing a tin-dioxide and palladium film onto the delay path through the mask. The SAW tag and deposited film can be annealed to gain room-temperature hydrogen sensitivity and reversibility. The annealing can be for approximately 5 minutes at a temperature of approximately 350° C.

The deposited the tin-dioxide and palladium film is a non-uniform $SnO_2$ and Pd film having a rapid, stable response to hydrogen gas. The tin-dioxide and palladium film can be a non-uniform approximately 250 Å $SnO_2$ film with approximately 20 Å Pd having a rapid, stable response to hydrogen gas that is deposited using a mask made from an approximately 150 μm thick copper foil with an approximately 250 μm aperture width to ensure that the signal was not buried in noise at maximum attenuation at approximately 915 MHz.

The distance between the aperture and the substrate can be approximately 2 mm. The deposition can be accomplished by evacuating the chamber to less than $3 \times 10^{-6}$ Torr, controlling a temperature of the substrate at approximately 60° C., and controlling an $O_2$ pressure of approximately $3 \times 10^{-5}$ Torr in the evacuated chamber. An electron beam evaporation can be used to deposit the tin-dioxide and palladium film onto the delay path and the tin-dioxide depositions were in a range of approximately 3 Å to approximately 5 Å per second for reproducibility.

A second embodiment provides a coded surface acoustic wave tag and hydrogen gas sensor that includes a substrate, a detector bank of reflectors fabricated at one end of the substrate to generate a detector surface acoustic wave in response to a interrogation signal, a reference bank of reflectors identical to the detector bank of reflectors fabricated at an opposite end of the substrate to generate a reference surface acoustic wave in response to the interrogation signal, a transducer fabricated on the substrate between the detector and reference banks of reflectors for receiving the interrogation signal and transmitting the detector and reference surface acoustic wave from the detector and the reference banks of reflectors in response, and a hydrogen gas sensor consisting of a tin dioxide ($SnO_2$) and palladium (Pd) film that is sensitive to hydrogen gas at ambient temperature deposited in a propagation delay path between the detector bank of reflectors and the transducer to modulate the detector surface acoustic wave propagation parameters in response to sensing a hydrogen gas.

In a preferred embodiment, the surface acoustic wave tag can be an orthogonal frequency coded surface acoustic wave identification tags for use in a multi-sensor environment. The detector and reference banks of reflectors can include plural sequential reflectors each having a frequency that is orthogonal in time and frequency to each other as an orthogonal frequency coded (OFC) surface acoustic wave tag. The surface acoustic wave tag can be a wireless tag sensor.

The surface acoustic wave tag can be a battery less tag sensor. The hydrogen sensor consists of a non-uniform $SnO_2$ and Pd film having a rapid, stable response to hydrogen gas, and in a preferred embodiment, the $SnO_2$ and Pd film can be a non-uniform approximately 250 Å $SnO_2$ film with approximately 20 Å Pd having a rapid, stable response to hydrogen gas.

A third embodiment provides a hydrogen gas sensing system that includes plural coded SAW tag sensors each include a bank of detector reflectors and an identical bank of reference reflectors, a transducer fabricated between the detector and reference banks of reflectors, a non-uniform tin-dioxide palladium sensor deposited in a propagation delay path between the detector bank of reflectors and the transducer to modulate the detector surface acoustic wave propagation parameters in response to hydrogen gas detection, and a transceiver to receive a surface acoustic wave from the SAW tag sensor in response to an interrogation signal and to correlate the received surface acoustic wave against a matched filter to produce two compressed pulses, one pulse unchanged on exposure to hydrogen gas while the other pulse exhibits changes insertion loss and delay due to am acoustoelectric interaction of hydrogen gas with the $SnO_2$—Pd film.

Further objects and advantages of this invention will be apparent from the following detailed description of preferred embodiments which are illustrated schematically in the accompanying drawings.

DESCRIPTION OF THE PREFERRED EMBODIMENTS

Figure 1:
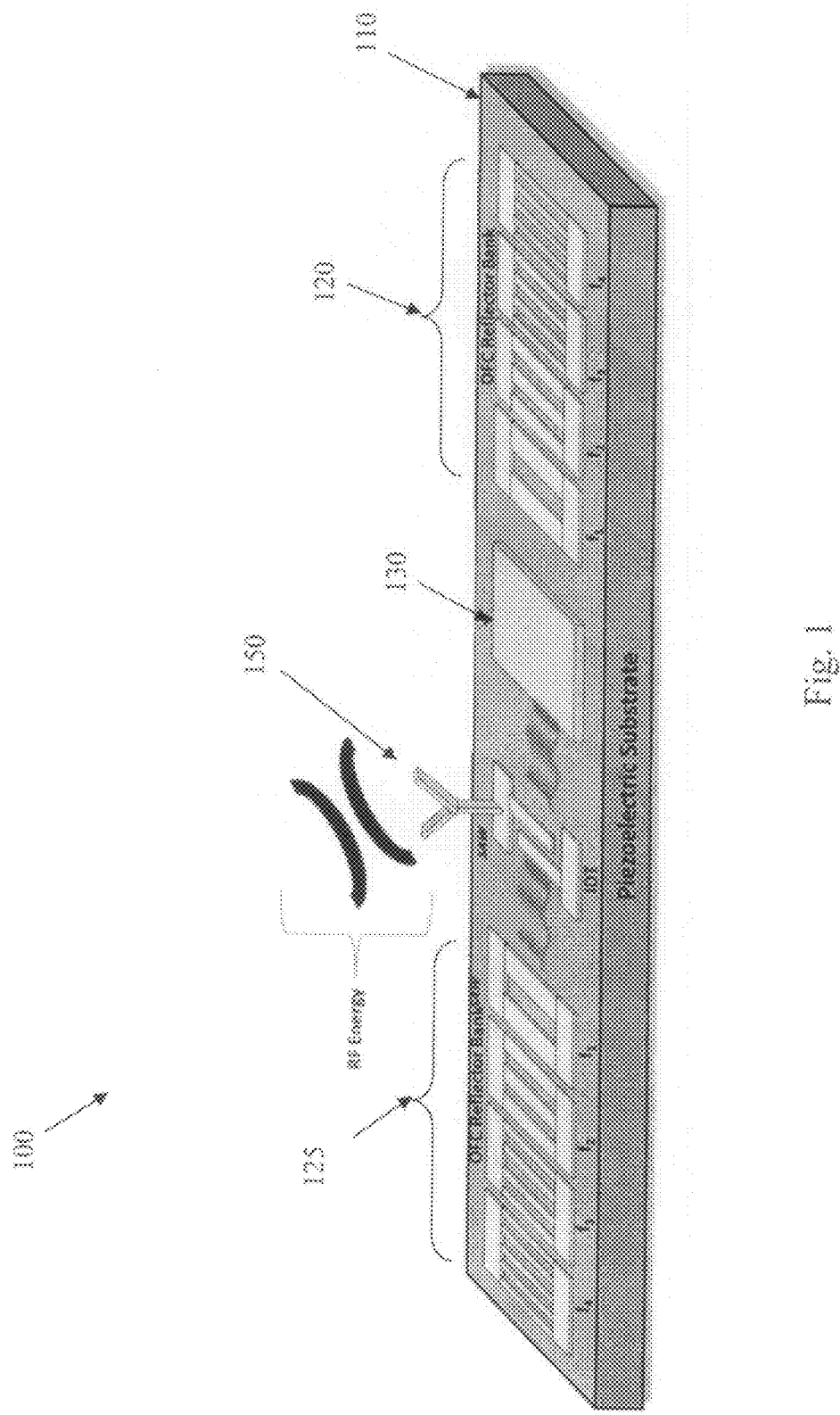
FIG. 1 is a perspective schematic diagram of a passive, wireless, orthogonal frequency coded surface acoustic wave identification tag sensor according to the present invention.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The following is a list of reference numerals used in the description and the drawings to identify components:
100 SAW device
110 piezoelectric substrate
120 OFC reflector bank
125 reference OFC reflector bank
130 H2 sensor
150 transducer
200 film deposition system
210 sample holder
220 SAW device
230 shadow mask
250 vaporized film molecules
260 crystal monitors
270 electron beam
280 metal source
290 feedthroughs Dr. Donald Malocha has completed research in the area of surface acoustic wave devices resulting in several issued U.S. Patents including U.S. Pat. Nos. 8,169,320; 7,961,105; 7,952,482; 7,825,805; 7,777,625; 7,642,898; and 7,623,037 and pending patent applications including U.S. Patent Pub. Nos. 2012/0174678 and 2011/0285510 each having a common inventor and assigned to the same assignee, and are each incorporated herein by reference in their entirety.

The orthogonal frequency coded surface acoustic wave (OFC-SAW) tag can be built on the commonly used YZ-lithium niobate (YZ—LiNbO3) piezoelectric substrate, a well-researched SAW device platform, and implements spread spectrum coding in order to achieve multiple-access capability to read multiple devices simultaneously.

In 2010 Dr. Donald Malocha and B. H. Fisher completed a study on the Aging of Ultra-Thin Palladium Films on SAW Hydrogen Gas Sensors at the University of Central Florida, School of Electrical Engineering and Computer Science and concluded that ultra-thin Pd films suffer from oxygen adsorption when exposed to ambient air. The results of the study provided promising solutions to the aging problem, such as encapsulation and film annealing. These solutions may accelerate the practical implementation of passive, wireless, SAW hydrogen gas sensors in various environments.

They also completed a study of the acoustoelectric effect of SAW sensors that was published March 2010, entitled Ultrasonics, Ferroelectrics and Frequency Control, IEEE Transactions that described Pd resistivity verses thickness characterization and the effects of the SAW-Pd thin film interaction with and without hydrogen exposure. For this study, a series of test devices were designed and fabricated.

SAW-thin-film acoustoelectric in-situ observations and measurements were described at the 2011 Joint conference if the IEEE International conference May 2-5, 2011 by Dr. Malocha and Brian Fisher. This paper presented the approach taken in configuring an electron beam evaporation system for ultra-thin-film characterization and the design of test fixtures, data acquisition configuration, and experimental procedures to extract and analyze SAW parameters in real time, and to extract the thin-film properties under test. The paper also mentioned the discrepancy in measurement due to non-uniform distribution of the film.

The in-situ test fixture was designed to be mechanically, thermally and electrically stable. Data was taken for many SAW devices and over a wide range of frequencies and the results showed that the use of the in-situ procedure yielded: good agreement between theoretical predictions and the measured data, allowed characterization of a SAW hydrogen gas sensor in real-time and allowed various different methods to be used to calibrate the film deposition system and procedure.

The thin-film acoustoelectric effect in surface acoustic wave devices describes the interaction of electrical energy between a SAW in a piezoelectric medium and a thin-film placed in the wave's propagation path. The real-time observation of the thin-film acoustoelectric interaction is useful in the design and characterization of SAW-based thin-film chemical and physical sensors such as temperature, humidity, viscosity, voltage, current, hall effects, and the like.

The present invention provides a wireless surface acoustic wave radio frequency device with a hydrogen gas sensor deposited on the delay path between the surface acoustic wave reflector bank and the transceiver. An embodiment provides methods for creating a tin dioxide ($SnO_2$) and palladium (Pd) thin-film stack that is sensitive to hydrogen gas at room temperature for use with the surface acoustic wave identification tags.

Another embodiment provides methods and devices for a wireless hydrogen gas sensor via the integration of the $SnO_2$—Pd film with the orthogonal frequency coded surface acoustic wave platform. Advantages of the methods, systems and devices include a low power or battery less, wireless surface acoustic wave radio frequency device with a hydrogen gas sensor that uses orthogonal frequency coding for use in a multi-tag system.

The first embodiment describes the creation of a passive (battery less), wireless, surface acoustic wave device with an integrated hydrogen gas sensor that utilizes a room-temperature hydrogen sensitive $SnO_2$—Pd film. In the preferred embodiment, the hydrogen gas sensors are built on a platform technology referred to as orthogonal frequency coded surface acoustic wave (OFC-SAW) radio frequency identification (RFID) tag sensors.

Orthogonal frequency coding the surface acoustic wave identification tags and sensors enables unique sensor identification for use in a multi-sensor environment. Orthogonal frequencies are used to spread the signal bandwidth. The orthogonality condition describes a relationship between the local chip frequencies and their bandwidths wherein the adjacent frequencies are not required to be sequential. The OFC-SAW tag is built on the commonly used YZ-lithium niobate (YZ—LiNbO3) piezoelectric substrate 110, a well-researched SAW device platform, and implements spread spectrum coding in order to achieve multiple-access capability to read multiple devices simultaneously. A more complete description of orthogonal frequency coding can be found in U.S. Pat. No. 7,642,898 and in D. C. Malocha, et al., "Orthogonal frequency coding for SAW device application," 2004 IEEE International Ultrasonics, Ferroelectrics, and Frequency Control 50.sup.th Anniversary Joint Conference, in press, which are incorporated herein by reference.

FIG. 1 is a perspective schematic diagram of a passive, wireless, orthogonal frequency coded surface acoustic wave identification tag hydrogen sensor 100 according to the present invention. In the example shown, the OFC reflector bank 120 is composed of sequential reflectors (called chips) with center frequencies from $f_1$ to $f_4$. The frequencies ($f_1$-$f_4$) are orthogonal in time and frequency to each other to minimize interference between chips as the SAW travels beneath the reflector bank. For hydrogen gas sensing, a Pd—$SnO_2$ film 130 is deposited in the delay path between the SAW transducer 150 and the frequency coded SAW reflector bank 120. Another identical reflector bank 125 on the other side of the SAW transducer 150 is used as a reference for sensing changes.

Figure 2:
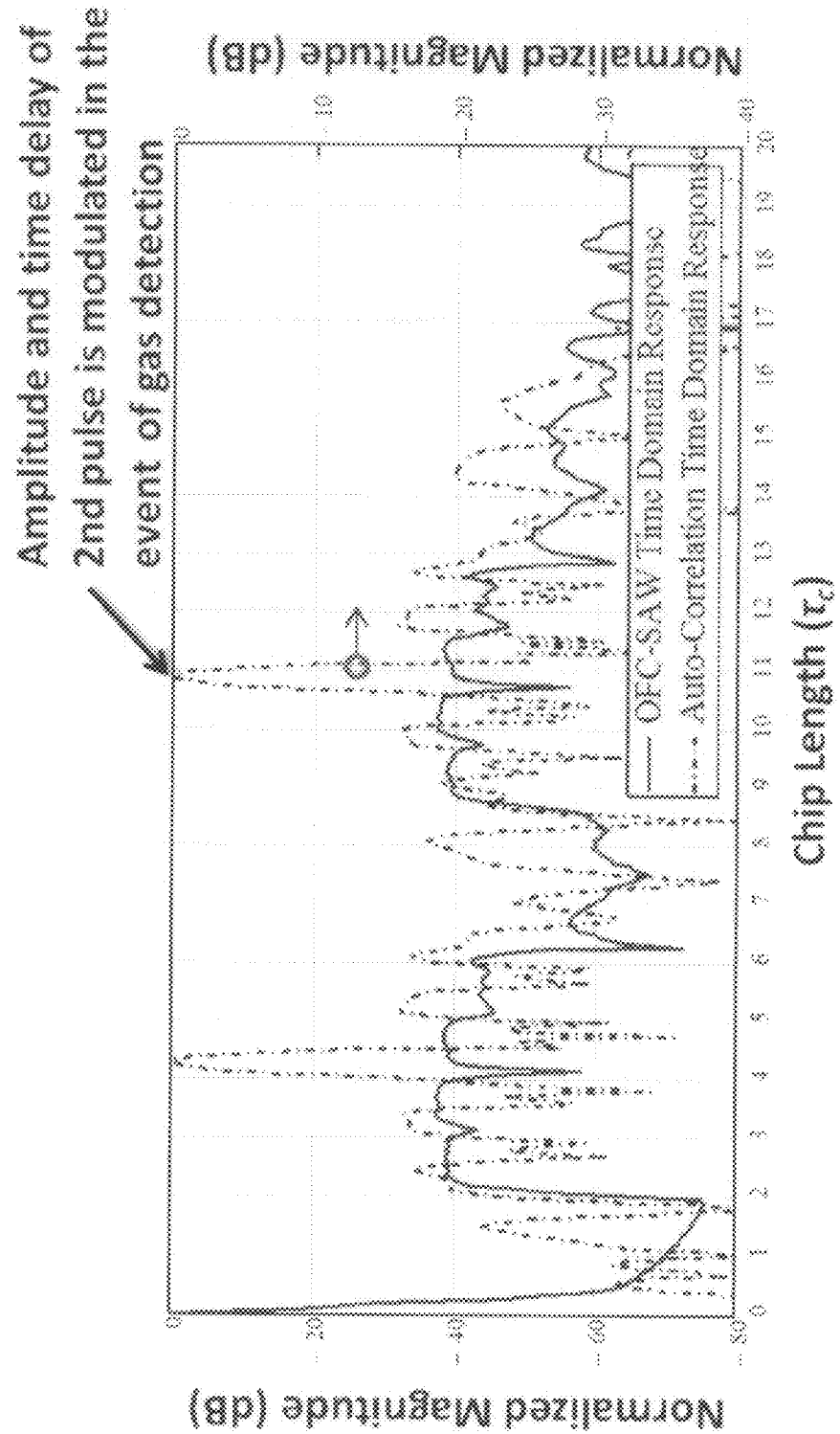
FIG. 2 shows the normalized magnitude (in dB) of an OFC SAW time domain response showing the modulation of a pulse in response to hydrogen gas detection.

The SAW propagation parameters are modulated by the presence and the properties of the chemically-sensitive thin-film and the amplitude and delay of the second correlation peak is modulated in the event of gas detection. The received OFC-SAW signal is correlated against a matched filter producing two compressed pulses; one pulse remains unchanged on exposure to hydrogen gas, while the other exhibits changes in insertion loss and delay, due to acoustoelectric interaction of hydrogen gas with the Pd—$SnO_2$ film and the SAW as shown in FIG. 2.

Figure 3:
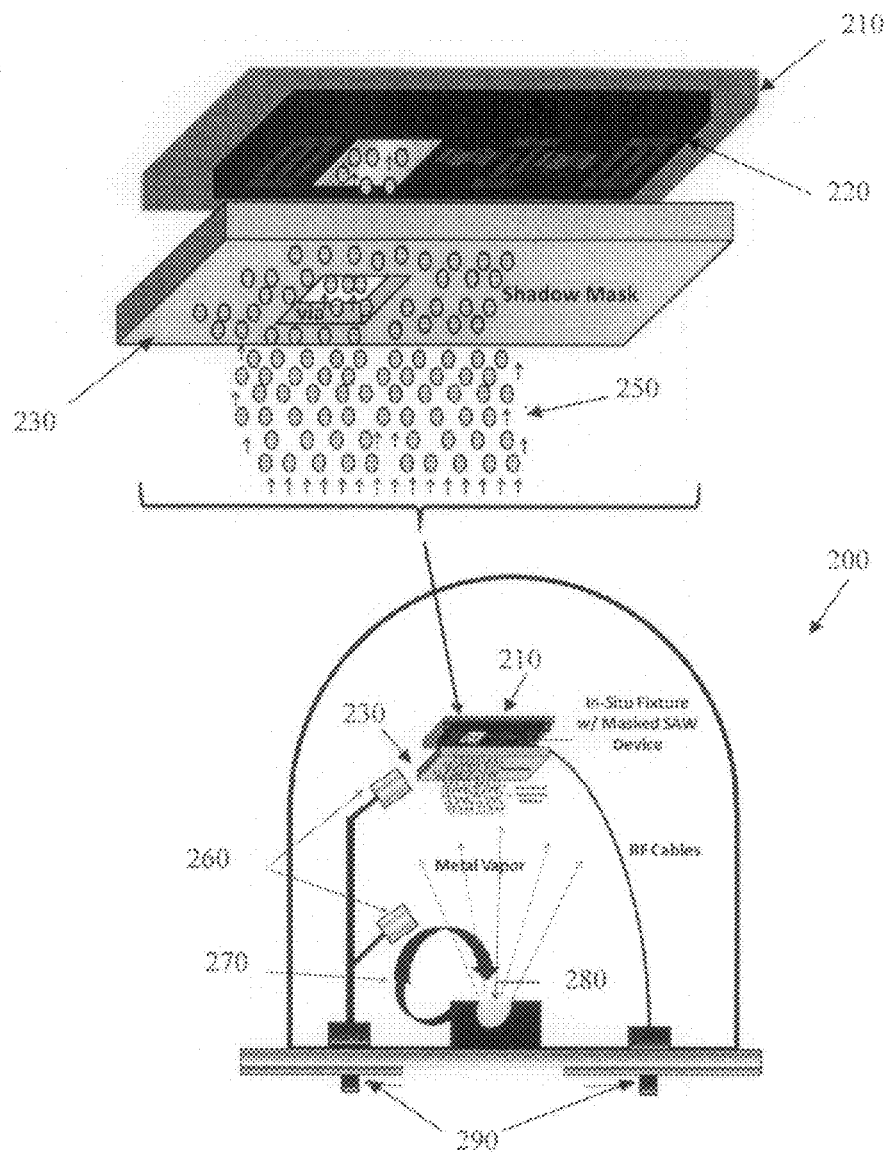
FIG. 3a shows a schematic of the in-situ fixture with a masked surface acoustic wave device inside the e-beam film disposition system.
FIG. 3b is an exploded view of the surface acoustic wave device, shadow mask and the evaporation film molecules.

A second embodiment describes the development of a room-temperature hydrogen sensitive tin dioxide ($SnO_2$) and palladium (Pd) film. FIG. 3a shows a schematic of the in-situ fixture 200 with a masked SAW device 220 inside the electron-beam film disposition system 200, with dual quartz crystal monitors 260, and high-vacuum RF feed through 290.

FIG. 3b is an exploded view of the SAW device 220 on the sample holder 210 connected with an RF cable, shadow mask 210 and the evaporation film molecules 250. As shown, an electron beam 270 is applied to the source metal causing metal vapors directed toward the masked saw device 220.

The growth and processing of the Pd—SnO2 is critical to its reversibility, sensitivity and room-temperature operation when exposed to hydrogen gas. Pd—$SnO_2$ with non-uniform thickness profiles were created by vapor deposition through a shadow mask as shown in FIG. 3a and annealed for approximately 5 min at approximately 350° C. in order to gain room-temperature hydrogen sensitivity and reversibility. The method produced a non-uniform approximately 250 Å $SnO_2$ film with approximately 20 Å Pd having a rapid, stable response to hydrogen gas.

The shadow mask was made from an approximately 150 μm thick copper foil with an approximately 250 μm aperture width to ensure that the signal was not buried in noise at maximum attenuation at 915 MHz. The distance between the aperture and the substrate is approximately 2 mm. Experimentation on films of uniform thickness-profiles failed to produce the long-term stability. Hydrogen sensitivity and reaction rates were observed in the non-uniform film profiles.

$SnO_2$ film depositions were performed using an electronic beam evaporator with 99.9% pure pellets, which were purchased from Kurt J Lesker Company. The material was evaporated from an $Al_2O_3$ crucible liner using approximately 10 kV and approximately 28 to 32 mA of current. The evaporation current was relatively low because $SnO_2$ sublimes and creates very high deposition rates at relatively low currents. High deposition rates are known to create porous films which are desired for gas sensing but provide poor control over the desired thickness.

The $SnO_2$ depositions were kept in a range between approximately 3 to 5 Å/s to ensure reproducibility. A substrate temperature controller and oxygen gas injection were used on the ebeam system to control the deposition environment as precisely as possible. Elevating the substrate temperature has the added benefit of desorbing surface adsorbed molecules that survive the substrate cleaning process.

The substrate temperature was controlled at approximately 60° C. and an oxygen pressure of approximately $3\times10^{-5}$ Torr was introduced after the chamber was evacuated to less than approximately $3\times10^{-6}$ Torr. The $O_2$ gas was evacuated before the Pd ultra-thin film (UTF) was evaporated. For the purposes in the experiment, the Pd UTF film needed to be as porous as possible, thus the slowest stable growth attainable of approximately 0.1 Å/s was used. The Pd UTF film was evaporated from a tungsten crucible liner using approximately 10 kV and approximately 35 to approximately 40 mA of current.

Figure 4:
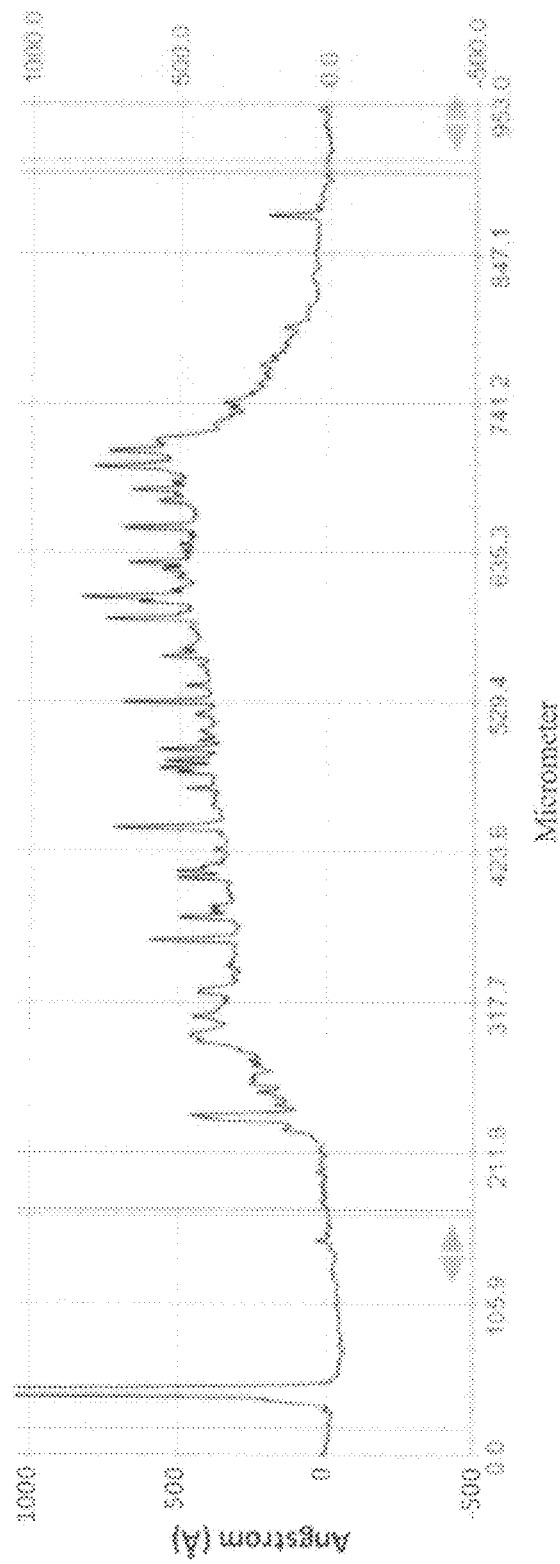
FIG. 4 shows a non-uniform film thickness profile after deposition through a shadow mask.

After deposition and annealing the film's thickness profile was measured using Veeco Dektak Stylus profilometer. FIG. 4 shows an approximately 500 Å SnO2+20 Å Pd film thickness profile after deposition through an approximately 0.5 mm aperture shadow mask. The film thickness profile was found to be non-uniform as shown in FIG. 4. The slope in the side walls were found to follow a Gaussian distribution and the top was flat. The packaged sensor die was solder to a planar 915 MHz folded dipole antenna.

Figure 5:
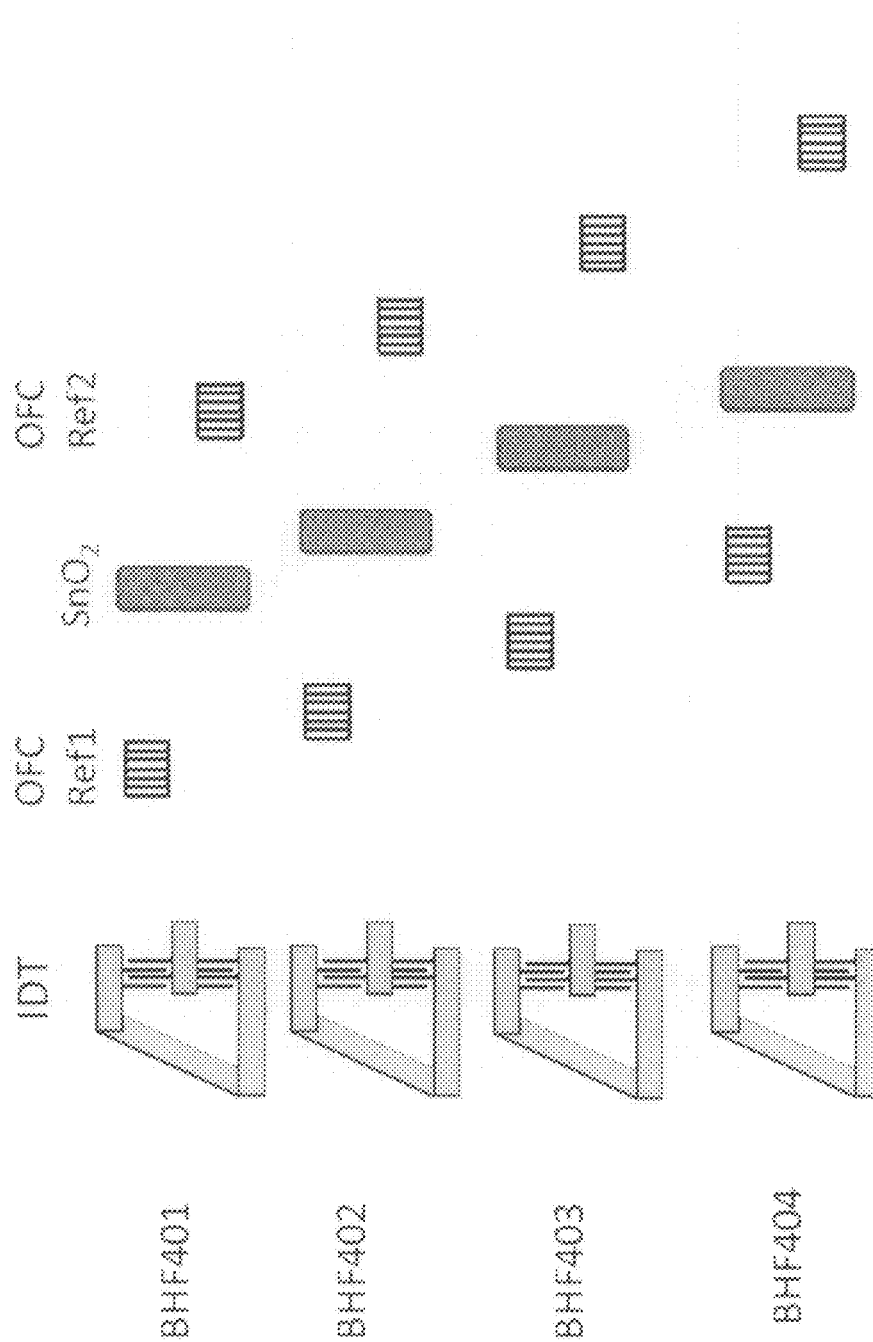
FIG. 5 is a schematic showing four different orthogonal frequency codes.

FIG. 5 is a schematic of four different OFC-SAW codes, labeled as BF401 through BF404 that were created for testing. The three devices labeled BHF402, BF403 and BHF404 where simultaneously interrogated from a distance of approximately 1.5 feet while they were exposed to various flow rates of 2% $H_2$, 98% $N_2$ gas. For the experiment, three sensors were placed directly above the gas flow tubes to benefit from the buoyancy of hydrogen gas and to increases the chances of exposure at low flow rates.

The transmitting/receiving (Tx/Rx) antenna was placed above the sensors. In the absence of a gas mixing equipment the sensors were exposed to various flow rates of hydrogen gas. This is equivalent to exposing the film to various concentrations of hydrogen gas because the number of hydrogen molecules that react with $SnO_2$ changes with flow rate and gas concentration. The change in propagation loss and the fractional change in group delay of the sensors BF402, BF403 and BF404 are plotted in FIG. 6a. Upon exposure to 2% H2 98% N2 gas there was a 10 dB (BHF402) to 15 dB (BHF403 & BHF404) increase in propagation loss in the devices. BHF402 is used to determine the amplitude sensitivity because BHF403 and BHF404 become saturated at relatively low flow rates.

Figures 6A, 6B:
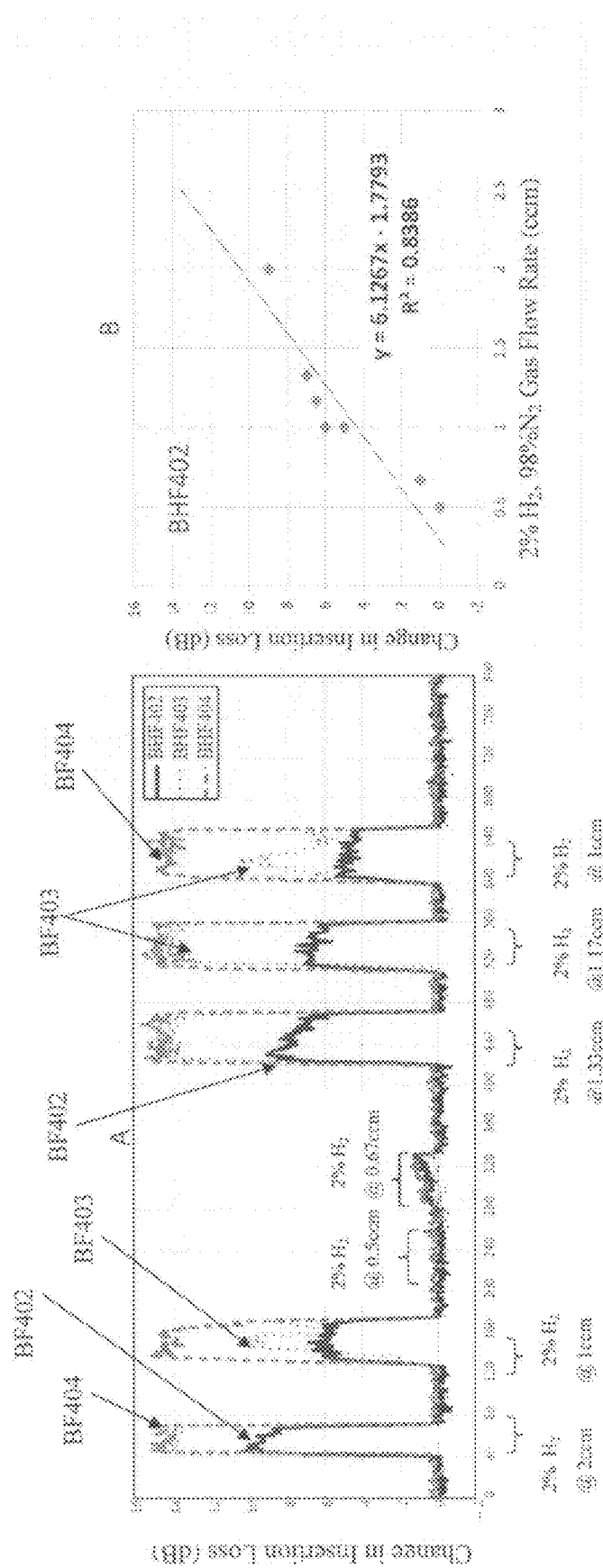
FIG. 6a shows a plot of the change in propagation loss as a function of time for 3 passive wireless OFC-SAW devices.
FIG. 6b is a plot showing the linear relationship between the change in insertion loss as a function of hydrogen gas flow rate.
Figure 7:
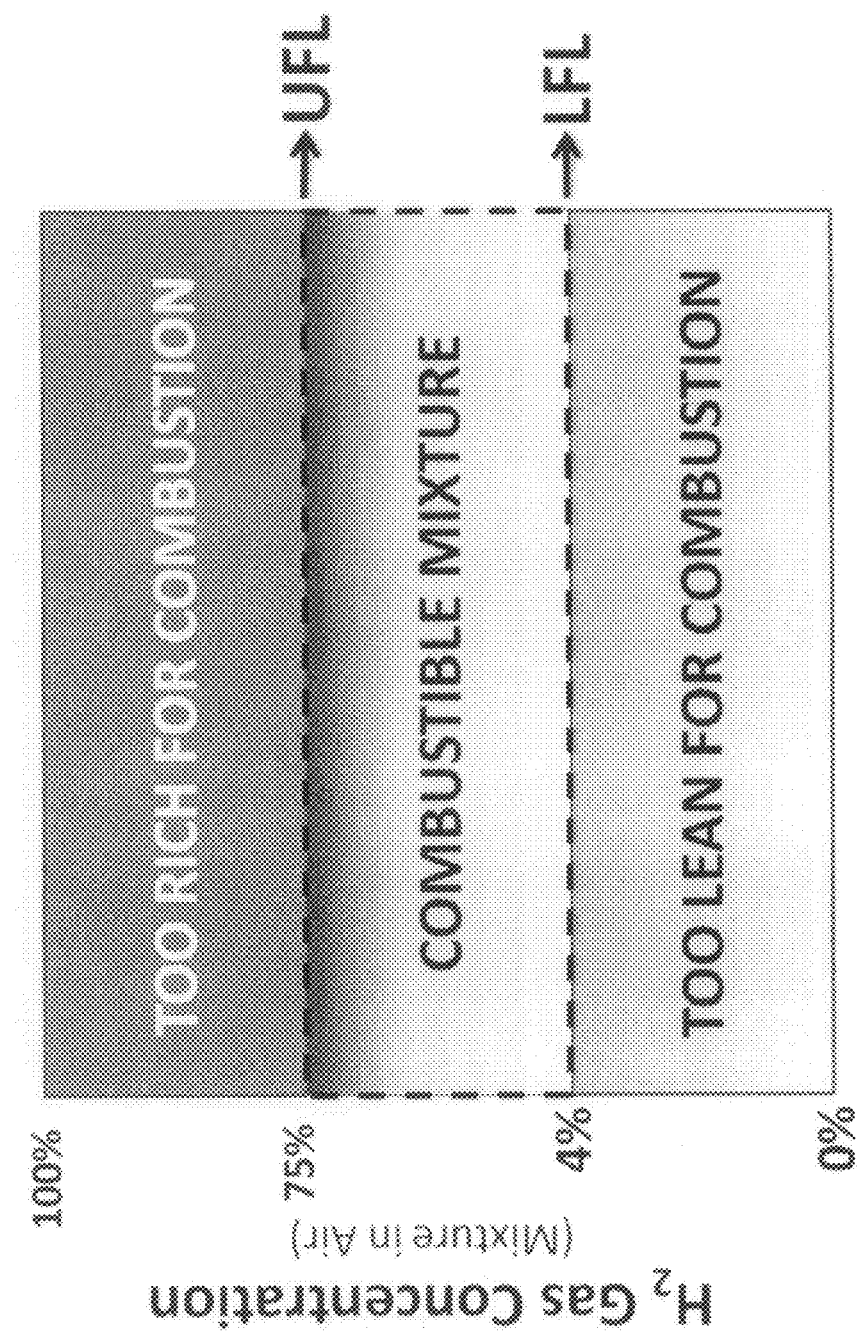
FIG. 7 shows the upper and lower flammability limits of hydrogen by volume in air.

FIG. 6b is a plot of the change in propagation loss as a function of the flow rate of 2% H2 98% N2 gas. It shows a linear relationship between the change in propagation loss as a function of gas flow rate for BHF402. This shows that the sensors can have a linear response to various concentrations of hydrogen gas. Given the high fractional change at relatively low flow rates, the sensors may utilized for low concentrations (in hundreds of ppm range) of hydrogen in order to prevent saturation and to observe a linear response.

Referring back to FIG. 1, the Pd—SnO$_2$ film 130 just described is deposited in the delay path between the SAW transducer 150 and the frequency coded SAW reflector bank 120. The SAW propagation parameters are modulated by the presence and the properties of the chemically-sensitive Pd—SnO$_2$ film and the amplitude and delay of the second correlation peak is modulated when hydrogen gas is detected. The received orthogonally coded surface acoustic wave signal is correlated against a matched filter producing two compressed pulses; one pulse remains unchanged on exposure to hydrogen gas, while the other exhibits changes in insertion loss and delay, due to acoustoelectric interaction of hydrogen gas with the Pd—SnO$_2$ film and the SAW as shown in FIG. 2.

The methods and devices of the present invention can be used to make wireless distributed measurements of the presence and concentration of hydrogen gas in an area. The U.S. Department of Energy has expressed a need for high-temperature selective gas sensors for down-stream process monitoring of hydrogen gas in fossil energy power systems.

Areas having an existing need for the sensors according to the present invention are in nuclear reactors containment buildings, oil refineries, coal mines, and process plants. Within the energy industry, power transmission and distribution equipment would benefit from continuous distributed monitoring since power transmission and distribution equipment failure is typically preceded by temperature anomalies and discharge of gaseous hydrocarbons. This can result in higher efficiency and lower costs to the consumer. The nuclear power industry has also expressed interest in the use of radiation hard passive wireless hydrogen gas sensor networks in reactor containment tanks. Excessive hydrogen levels can be used to indicate depletion of the cooling water. NASA has also expressed needs for passive wireless hydrogen gas sensing networks that can determine the concentration of location of a gas leak at various ground support and research facilities.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A gas sensor system comprising:
    a substrate;
    a coded surface acoustic wave (SAW) tag on said substrate, said SAW tag including:
        a detector bank of reflectors fabricated at one end of the substrate to generate a detector surface acoustic wave in response to an interrogation signal;
        a reference bank of reflectors identical to the detector bank of reflectors fabricated at an opposite end of the substrate to generate a reference surface acoustic wave in response to the interrogation signal;
        a transducer fabricated on the substrate between the detector and reference banks of reflectors for receiving the interrogation signal and transmitting the detector and reference surface acoustic wave from the detector and the reference banks of reflectors in response;
    a hydrogen gas sensor on said substrate comprising a tin dioxide (SnO$_2$) film with a palladium (Pd) film thereon that is sensitive to hydrogen gas in a propagation delay path between the detector bank of reflectors and the transducer to modulate the detector surface acoustic wave propagation parameters in response to sensing the hydrogen gas.

2. The system of claim 1 wherein the
    reference bank of reflectors and the detector bank of reflectors each provide a plurality of center frequencies to implement orthogonal frequency coded (SAW) identification for use in a multi-sensor environment.

3. The system of claim 2 wherein the detector and reference banks of reflectors comprises:
    plural sequential reflectors each having a frequency that is orthogonal in time and frequency to each other as an orthogonal frequency coded (OFC) surface acoustic wave tag.

4. The system of claim 1 wherein the surface acoustic wave (SAW) tag is a wireless tag sensor.

5. The system of claim 1 wherein the SAW tag is a battery less tag sensor.

6. The system of claim 1 wherein the modulation of the detector SAW propagation parameters comprise:
    modulation of an amplitude and delay of a second correlation peak of the detector surface acoustic wave in the event of hydrogen gas detection.

7. The system of claim 1 wherein the hydrogen gas sensor is created by vapor deposition through a shadow mask.

8. A gas sensing system comprising:
    a plurality of coded surface acoustic wave (SAW) tag sensors each comprising:
        a bank of detector reflectors and an identical bank of reference reflectors;
        a transducer fabricated between the detector and reference banks of reflectors;
        a tin-dioxide film having a palladium film thereon (SnO$_2$—Pd film) in a propagation delay path between the detector bank of reflectors and the transducer to modulate the detector surface acoustic wave propagation parameters in response to hydrogen gas detection; and
    a transceiver to receive a surface acoustic wave from the SAW tag sensor in response to an interrogation signal and to correlate the received surface acoustic wave against a matched filter to produce two compressed pulses, one pulse unchanged on exposure to hydrogen gas while the other pulse exhibits changes in insertion loss and delay due to an acoustoelectric interaction of the hydrogen gas with the SnO$_2$—Pd film.

* * * * *